(12) United States Patent
McCormick et al.

(10) Patent No.: US 12,421,348 B2
(45) Date of Patent: Sep. 23, 2025

(54) COATING COMPOSITIONS AND METHODS WITH POLYFUNCTIONAL CARBAMATE SALT

(71) Applicant: SWIMC LLC, Cleveland, OH (US)

(72) Inventors: Nathan McCormick, Ham Lake, MN (US); Jason Lindquist, Lino Lakes, MN (US)

(73) Assignee: SWIMC LLC, Cleveland, OH (US)

( * ) Notice: Subject to any disclaimer, the term of this patent is extended or adjusted under 35 U.S.C. 154(b) by 608 days.

(21) Appl. No.: 17/753,607

(22) PCT Filed: Sep. 9, 2020

(86) PCT No.: PCT/US2020/049854
§ 371 (c)(1),
(2) Date: Mar. 9, 2022

(87) PCT Pub. No.: WO2021/055195
PCT Pub. Date: Mar. 25, 2021

(65) Prior Publication Data
US 2022/0332884 A1    Oct. 20, 2022

Related U.S. Application Data

(60) Provisional application No. 62/902,049, filed on Sep. 18, 2019.

(51) Int. Cl.
| | | |
|---|---|---|
| C08G 18/79 | (2006.01) | |
| C07C 211/63 | (2006.01) | |
| C08G 18/28 | (2006.01) | |
| C09D 5/08 | (2006.01) | |
| C09D 7/65 | (2018.01) | |

(52) U.S. Cl.
CPC .......... C08G 18/792 (2013.01); C07C 211/63 (2013.01); C08G 18/285 (2013.01); C09D 5/08 (2013.01); C09D 7/65 (2018.01); C08G 2150/90 (2013.01)

(58) Field of Classification Search
CPC .... C08G 18/792; C08G 2150/90; C09D 5/08; C09D 7/65
See application file for complete search history.

(56) References Cited

U.S. PATENT DOCUMENTS

| | | |
|---|---|---|
| 2,187,719 A | 1/1940 | Williams |
| 4,296,215 A | 10/1981 | Markiewitz |
| 4,602,061 A | 7/1986 | Akkerman |
| 5,132,367 A | 7/1992 | Chan |
| 5,288,802 A | 2/1994 | Walters et al. |
| 5,512,639 A * | 4/1996 | Rehfuss ............... C09D 175/04 525/509 |
| 5,567,761 A | 10/1996 | Song |
| 6,740,359 B2 | 5/2004 | Kumar et al. |
| 7,396,429 B2 | 7/2008 | Beckley et al. |
| 8,962,725 B2 | 2/2015 | Brinkhuis et al. |
| 9,718,988 B2 * | 8/2017 | Brinkhuis ............ B01J 31/0205 |
| 10,870,763 B2 | 12/2020 | Wehner et al. |
| 10,876,007 B2 | 12/2020 | Wehner et al. |
| 2006/0078742 A1 | 4/2006 | Kauffman et al. |
| 2014/0220252 A1* | 8/2014 | Brinkhuis ............ B01J 31/0205 524/502 |
| 2018/0000720 A1* | 1/2018 | Ijdo ...................... A61K 8/8152 |
| 2018/0094143 A1 | 4/2018 | Wehner et al. |
| 2018/0163081 A1 | 6/2018 | Goedegebuure et al. |
| 2018/0282554 A1 | 10/2018 | Avudaiappan et al. |
| 2019/0031814 A1* | 1/2019 | Hegedus ............... C08G 18/423 |
| 2021/0139624 A1 | 5/2021 | Lindquist et al. |

FOREIGN PATENT DOCUMENTS

| | | |
|---|---|---|
| CN | 1646572 | 7/2005 |
| CN | 102834436 | 12/2012 |
| CN | 102834437 | 12/2012 |
| CN | 102844361 | 12/2012 |
| CN | 107667151 | 2/2018 |
| CN | 109475574 | 3/2019 |
| EP | 3085748 | 12/2017 |
| JP | S60-231719 | 11/1985 |
| JP | 2011-037948 | 2/2011 |
| JP | 2012-180464 | 9/2012 |
| JP | 2016050260 | 4/2016 |
| WO | 03/089479 | 10/2003 |
| WO | 2014031181 | 2/2014 |
| WO | 2018005077 | 1/2018 |
| WO | WO-2018005077 A1 * | 1/2018 ............ A61K 8/042 |

(Continued)

OTHER PUBLICATIONS

International Search Report for international application No. PCT/US2020/049854, dated Nov. 11, 2020 (5 pages).

(Continued)

*Primary Examiner* — Mark S Kaucher

(57) ABSTRACT

A latent base catalyst and compositions and methods involving latent base-catalyzed Michael addition reaction are described herein. The described latent base catalyst is a substituted carbamate salt. The compositions described herein are derived from a Michael addition reaction and provide coatings, including primer coatings and direct-to-metal coatings, which have optimal potlife and cure response, and also demonstrate optimal adhesion, corrosion resistance, and weatherability when applied to a substrate and cured.

5 Claims, No Drawings

(56) References Cited

FOREIGN PATENT DOCUMENTS

WO     2018187430     10/2018
WO     2019217384     11/2019

OTHER PUBLICATIONS

Written Opinion for international application No. PCT/US2020/049854, dated Nov. 11, 2020 (5 pages).
R. Brinkhuis et al., "Taming the Michael Addition Reaction," European Coatings Journal, May 2015 (7 pages).
C. Perinu et al., "NMR Speciation of Aqueous MAPA, Tertiary Amines, and Their Blends in the Presence of CO2: Influence of pKa and Reaction Mechanisms," Ind. Eng. Chem. Res. (2018) vol. 57, p. 1337-1349.
A. Hartono et al., "Qualitative Determination of Species in DETA-H2O-CO2 System using 13C NMR Spectra," Ind. Eng. Chem. Res. (2007) vol. 46, p. 249-254.
Extended European Search Report issued for European patent appl. No. 20866208.0, dated Sep. 22, 2023 (12 pages).
First Office Action issued for Chinese patent appl. No. 202080058817.8, dated Oct. 26, 2023 (27 pages, including English translation).

\* cited by examiner

COATING COMPOSITIONS AND METHODS WITH POLYFUNCTIONAL CARBAMATE SALT

BACKGROUND

Coatings are frequently applied to various substrates, including metal and steel substrates to protect the substrate from corrosion, impact and other damage while also providing certain appearance or aesthetic features. Generally, these coatings are economical and relatively easy to apply. The coatings dry quickly and have good corrosion resistance and chemical resistance, making the coatings especially useful for coating metal components to be used over long periods of time and/or in corrosive environments.

Conventionally, many coating systems are crosslinkable two-component compositions, where the components are stored separately and mixed prior to use. The two components are highly reactive and will begin to crosslink as soon as they are mixed. It is conventional to include a catalyst in such primer coating systems to increase the rate of the crosslinking reaction between the two components.

The crosslinking reaction may be base-catalyzed or acid-catalyzed. Base-catalyzed systems are sometimes preferred because they are capable of rapid or fast cure. However, because of the rapid rate of cure, these compositions can only be used for a relatively short period of time after the components are mixed, defined as the potlife of the coating composition. In some base-catalyzed systems, viscosity increases so rapidly that the coating cures before it can be fully applied to a surface, and accordingly, these systems are of limited practical use.

Due to regulatory concerns regarding the use of volatile organic compounds (VOC) in solvent-borne coatings, high solids systems with low solvent content are preferred. However, high solids systems present several challenges with regard to balancing potlife and cure speed. For example, a high solids composition typically includes less solvent that can evaporate when the coating is applied, and as a result, the potlife is much lower than preferred. On the other hand, the increase in reaction rate when the coating is applied is also reduced with less solvent in the system, leading to slower cure. A combination of rapid cure and long potlife is therefore difficult to achieve for conventional high solids coating systems.

One possible solution to the problem of reduced potlife in base-catalyzed systems is the use of a latent catalyst. These catalysts provide a favorable balance between the speed of cure and potlife. Typically, these catalysts are minimally active until the coating is applied, and provide longer potlife without compromising cure speed. For example, the use of substituted carbonate salts as latent catalysts for a base-catalyzed system is described in U.S. Pat. No. 8,962,725, incorporated herein by reference.

However, it is not known whether coating compositions that use such latent catalyst systems may be used as primer compositions, particularly where superior weathering and durability is desired. Moreover, when some currently known base-catalyzed compositions are applied directly to metal substrates, particularly acidic or acid-treated substrates, a loss in corrosion resistance and/or adhesion is seen.

Other latent catalysts for base-catalyzed systems are also known, but their synthesis may include the formation of environmentally hazardous byproducts that must be eliminated to meet regulatory requirements. For example, the synthesis of a carbamate salt latent catalyst is described in U.S. Patent Pub. No. 20180000720, incorporated herein by reference, where a volatile amine byproduct is formed and must be removed to purify the product for optimal performance. The presence of the amine in the system can lead to unwanted side reactions such as, for example, rapid crosslinking that reduces potlife. Moreover, waste amine byproducts produced by the purification process may be environmentally hazardous.

Accordingly, there is a need for latent base catalysts that can take advantage of the rapid cure speed and optimal potlife demonstrated by latent base-catalyzed systems that crosslink via Michael addition reactions, and also produce coating compositions with optimal corrosion resistance and weathering properties. Additionally, there is a need for methods to synthesize latent base catalyst systems that are efficient and do not produce environmentally hazardous byproducts.

SUMMARY

The present description provides compositions and methods involving a Michael addition reaction catalyzed by a latent base catalyst. The compositions described herein are derived from a Michael addition reaction and provide coatings that have optimal potlife and optimal cure performance, and also demonstrate optimal weathering.

In one embodiment, the present description provides a latent base catalyst of the general formula (I). The catalyst is a substituted carbamate salt that is capable of reacting with at least one crosslinkable component of a crosslinkable resin composition.

In another embodiment, the present description provides a coating composition including at least one crosslinkable polymer that includes at least one crosslinkable resin component. The composition includes a latent base catalyst of the general formula (I), where the catalyst is a substituted carbamate salt that is capable of reacting with the at least one crosslinkable resin component. In an aspect, the latent catalyst is present in an amount of 0.001 to 1.0 meq based on the amount of the crosslinkable resin component. The coating composition demonstrates optimal potlife and optimal cure response.

In yet another embodiment, a method of preparing a latent base catalyst is provided. The method includes the steps of providing a hydroxide-functional component, and a component capable of reacting with the hydroxide-functional component to produce a latent base catalyst having the general formula (I).

In an embodiment, the present description provides a cured coating. The coating includes a polymer composition that includes a crosslinkable resin component and a latent catalyst of the general formula (I). After being applied to a substrate, the polymer coating composition cures in about 1 to 10 minutes at 150° F. (65.5° C.) to form the cured coating. As described herein, the cured coating demonstrates optimal weathering.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying drawings and the description below. Other features, objects, and advantages of the invention will be apparent from the description and drawings, and from the claims.

Selected Definitions

Unless otherwise specified, the following terms as used herein have the meanings provided below.

As used herein, the term "organic group" means a hydrocarbon group (with optional elements other than carbon and hydrogen, such as oxygen, nitrogen, sulfur, and silicon) that is classified as an aliphatic group, cyclic group, or combination of aliphatic and cyclic groups (e.g., alkaryl and aralkyl groups). The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, tetrabutyl (t-butyl), heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group or an aromatic group, both of which can include heteroatoms. The term "alicyclic group" means a cyclic hydrocarbon group having properties resembling those of aliphatic groups. The term "Ar" refers to a divalent aryl group (i.e., an arylene group), which refers to a closed aromatic ring or ring system such as phenylene, naphthylene, biphenylene, fluorenylene, and indenyl, as well as heteroarylene groups (i.e., a closed ring hydrocarbon in which one or more of the atoms in the ring is an element other than carbon (e.g., nitrogen, oxygen, sulfur, etc.)). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on. When such groups are divalent, they are typically referred to as "heteroarylene" groups (e.g., furylene, pyridylene, etc.)

A group that may be the same or different is referred to as being "independently" something. Substitution is anticipated on the organic groups of the compounds of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

The term "component" refers to any compound that includes a particular feature or structure. Examples of components include compounds, monomers, oligomers, polymers, and organic groups contained there.

The term "double bond" is non-limiting and refers to any type of double bond between any suitable atoms (e.g., C, O, N, etc.).

The term "triple bond" is non-limiting and refers to any type of triple bond between any suitable atoms.

"Michael addition," as used herein refers to the nucleophilic addition of a carbanion or other nucleophile to an electron-deficient ethylenically unsaturated compound, such as an α,β-unsaturated carbonyl compound, for example. The abbreviated form "MA" is used interchangeably herein with the term "Michael addition."

A Michael addition reaction follows the general reaction schematic shown here:

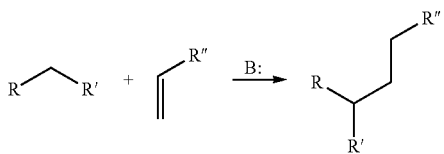

In the reaction schematic shown above, B is a latent base catalyst that reacts with the Michael addition (MA) donor by deprotonation to form a carbanion for a subsequent addition reaction with the MA acceptor.

The term "resin composition," as used herein refers to the resin-containing portion of the composition. The resin composition may include one or more resins or polymer compositions. Suitable examples include, without limitation, MA donors, MA acceptors, non-functional resins, and resins with functionality other than those required Michael addition. The term is used interchangeably herein with "polymer" or "polymer composition." As used herein, a resin or polymer composition may include one or more resin components.

By "Michael addition acceptor" or "MA acceptor" is meant a molecule having at least one MA acceptor functional group By "Michael addition donor" or "MA donor" is meant a molecule having at least one MA donor functional group.

By "MA acceptor/donor" is meant a molecule having at least one Michael addition (MA) acceptor functional group and at least one Michael addition (MA) donor functional group.

The term "crosslinker" refers to a molecule capable of forming a covalent linkage between polymers or between two different regions of the same polymer. A particular component is termed "crosslinkable" if it can react with another component via a crosslinking reaction, either via a self-crosslinking reaction or through the reaction of two or more polymers or between two different regions of the same polymer.

The term "self-crosslinking," when used in the context of a self-crosslinking polymer, refers to the capacity of a polymer to enter into a crosslinking reaction with itself and/or another molecule of the polymer, in the absence of an external crosslinker, to form a covalent linkage therebetween. Typically, this crosslinking reaction occurs through reaction of complimentary reactive functional groups present on the self-crosslinking polymer itself or two separate molecules of the self-crosslinking polymer.

The term "dispersion" in the context of a dispersible polymer refers to the mixture of a dispersible polymer and a carrier. The term "dispersion" is intended to include the term "solution."

The term "on", when used in the context of a coating applied on a surface or substrate, includes both coatings applied directly or indirectly to the surface or substrate. Thus, for example, a coating applied to a primer layer overlying a substrate constitutes a coating applied on the substrate.

The term "dry to handle," as used herein, refers to the stage of the coating process of a substrate wherein an applied coating is sufficiently cured to move on to the next stage of the manufacturing process.

Unless otherwise indicated, the term "polymer" includes both homopolymers and copolymers (i.e., polymers of two or more different monomers).

The term "comprises" and variations thereof do not have a limiting meaning where these terms appear in the description and claims.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a coating composition that comprises "an" additive can be interpreted to mean that the coating composition includes "one or more" additives.

Also herein, the recitations of numerical ranges by endpoints include all numbers subsumed within that range (e.g., 1 to 5 includes 1, 1.5, 2, 2.75, 3, 3.80, 4, 5, etc.). Furthermore, disclosure of a range includes disclosure of all subranges included within the broader range (e.g., 1 to 5 discloses 1 to 4, 1.5 to 4.5, 1 to 2, etc.).

DETAILED DESCRIPTION

The present description provides a latent base catalyst, methods of making such a catalyst and coating compositions for a variety of substrates including metal substrates and steel substrates. Specifically, the present description provides coating compositions for untreated or pretreated substrates, including, for example, steel substrates, where the coatings are derived from components that cure via a Michael addition reaction catalyzed by the latent base described herein.

The present description provides a latent base catalyst. In an aspect, the latent base catalyst is a substituted carbamate salt having the structure of general formula (I):

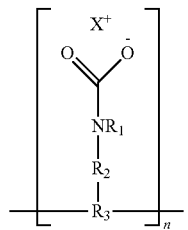

where:
each $X^+$ is independently a non-acidic cation;
each $R_1$ is independently H, C1 to C10 alkyl, aryl, aralkyl, or C1 to C10 substituted alkyl, aryl, aralkyl, or mixture or combinations thereof;
each $R_2$ and $R_3$ is each independently C1 to C10 alkyl, aryl, aralkyl, or C1 to C10 substituted alkyl, aryl, aralkyl, or mixture or combinations thereof; and
n is greater than 1.

The latent base catalyst having the structure in general formula (I) is capable of reacting with at least one crosslinkable component of a crosslinkable polymer or resin composition.

Without limiting to theory, it is believed that the latent base catalyst of general formula (I) functions by releasing carbon dioxide when the carbamate salt decomposes on application to a substrate as a wet film. In a closed pot, this reaction takes place slowly, allowing for extended pot life. When the coating is applied, and surface area increases, the base is regenerated quickly as carbon dioxide escapes from the surface, allowing for faster cure (i.e. drying and hardness development) of the coating. Accordingly, the use of a latent base catalyst of general formula (I) allows for optimal potlife, open time, and cure performance for the crosslinkable coating compositions described herein.

In the latent base catalyst having the structure of general formula (I), $X^+$ is a non-acidic cation. Where n in formula (I) is greater than 1, each $X^+$ in one unit of the latent base catalyst may be the same or different than $X^+$ in another unit of the same latent base catalyst molecule.

Suitable examples include, without limitation, alkali metal ion, alkali-earth metal ion, ammonium ion, phosphonium ion, and the like. In a preferred aspect, $X^+$ is a lithium, sodium, or potassium ion, and the like. More preferably, $X^+$ is a quaternary ammonium ion $NR'_4$ or a phosphonium ion $PR'_4$, wherein R is H, unsubstituted C1-C10 alkyl, aryl, aralkyl, substituted C1-C10 alkyl, aryl, aralkyl, and mixtures or combinations thereof. In a preferred aspect, R is an unsubstituted alkyl group having 1 to 4 carbon atoms. If the R group is substituted, the substituents are selected to not substantially interfere with the crosslinking reaction. In an aspect, to avoid interference with the action of the base catalyst, acidic substituents, such as for example, carboxylic acid substituents are present in only insubstantial amounts, or absent altogether.

In the latent base catalyst of general formula (I), $R_1$ is hydrogen, C1 to C10 alkyl, aryl, aralkyl, or C1 to C10 substituted alkyl, aryl, aralkyl, or mixture or combinations thereof. In a preferred aspect, $R_1$ is hydrogen.

In the latent base catalyst of general formula (I), $R_2$ and $R_3$ are each independently C1 to C10 alkyl, aryl, aralkyl, or C1 to C10 substituted alkyl, aryl, aralkyl, or mixture or combinations thereof. In a preferred aspect, R2 and R3 are each independently an unsubstituted alkyl group having 1 to 4 carbon atoms, more preferably 4 carbon atoms.

The latent catalyst described herein is a substituted carbamate salt synthesized by the reaction of a hydroxide-functional component with a component capable of reacting with the hydroxide-functional component. In an aspect, the hydroxide-functional component is a hydroxide base and the component capable of reacting with the hydroxide base is a multifunctional isocyanate.

Suitable hydroxide bases for use in the methods described herein include, without limitation, tetrahexylammonium hydroxide, tetradecyl-(i.e.C14)-trihexylammonium-hydroxide and tetradecylammonium hydroxide, tetrabutylammonium hydroxide, benzyltrimethylammonium hydroxide, or trihexylmethylammonium hydroxide or trioctylmethylammonium hydroxide, and mixtures or combinations thereof.

To prepare the latent base catalyst as described herein, the hydroxide-functional component is reacted with a multifunctional isocyanate. Suitable multifunctional isocyanate compounds include, without limitation, 2,4-toluenediisocyanate, hexamethylenediisocyanate (HDI), polymethylenepolyphenyl diisocyanate, methylenediphenyldiisocyanate, cyclic trimers, cocyclic trimers, homopolymers, copolymers, or mixtures thereof. In a preferred embodiment, the multifunctional isocyanate is a trimer. Examples of suitable trimers include, without limitation, trimerization products prepared from on average three diisocyanate molecules or a trimer prepared from on average three moles of diisocyanate (e.g., HDI) reacted with one mole of another compound such as, for example, a triol (e.g., trimethylolpropane). In a preferred aspect, the multifunctional isocyanate is HDI trimer.

The reaction of the hydroxide-functional component with a multifunctional isocyanate may be conduced in the presence of alcohol, such as methanol, for example. Without limiting to theory, when the reaction is conducted in the presence of alcohol, any isocyanate that did not react with hydroxide is believed to have reacted with an excess of methanol in solution. However, reaction in the presence of alcohol is not required, and the alcohol may be added at the end of the synthesis, i.e. after the hydroxide-functional component has reacted with the multifunctional isocyanate.

The latent catalyst described herein is a carbamate salt made by the reaction of a hydroxide base, preferably tetrabutyl ammonium hydroxide with a multifunctional isocyanate, preferably a trimer of HDI. In an aspect, the latent catalyst described herein includes more than one carbamate moiety, preferably two or more carbamate moieties. In an aspect, the ratio of hydroxide groups to isocyanate groups in the latent catalyst is from 0.60:1.0 to 0.99:1.0, preferably 0.7:1.0 to 0.99:1.0. More preferably, the latent catalyst has a ratio of hydroxide groups to isocyanate groups of 0.9:1.0, i.e. the catalyst has an index of 0.9 relative to the amount of isocyanate groups present. Any excess isocyanate in the system that did not react with hydroxide will react with excess methanol, water, or other solvents present in solution.

In a preferred aspect, the latent base catalyst described is prepared by the reaction of tetrabutyl ammonium hydroxide (TBAH) with hexamethylene diisocyanate. This latent base catalyst has the structure shown in Formula (II).

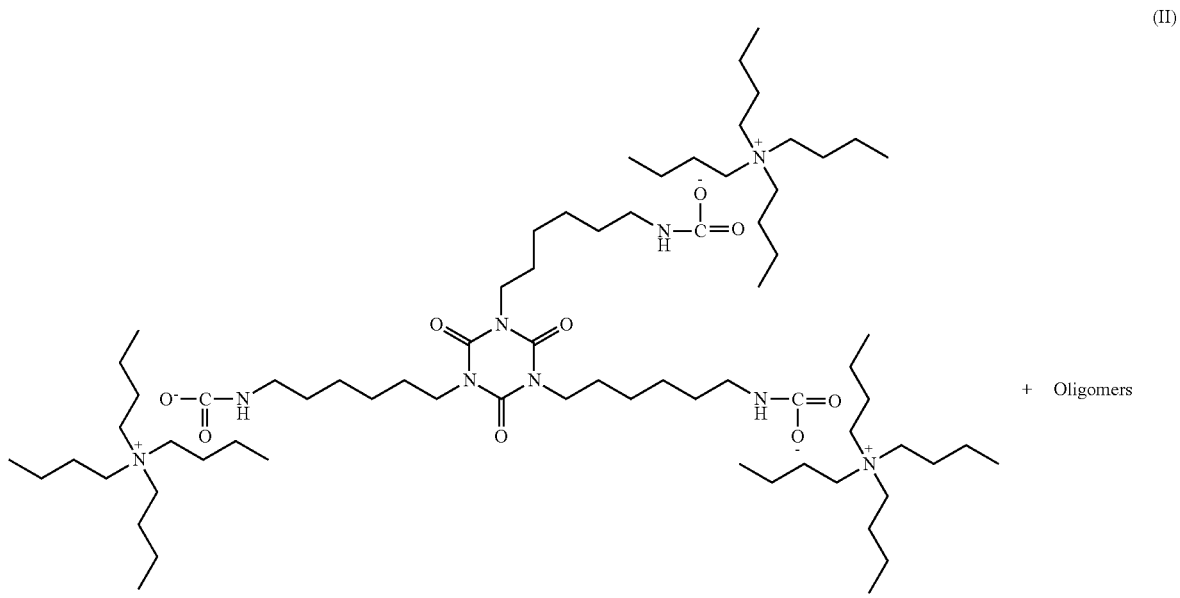

(II)

+ Oligomers

In an embodiment, the latent catalyst described herein is a carbamate salt made by the reaction of a hydroxide base with a multifunctional isocyanate, where the reaction is overindexed on the multifunctional isocyanate. That is, the reaction includes excess isocyanate to ensure complete conversion of the hydroxide to carbamate. Any excess isocyanate remaining after reaction is consumed by with excess methanol, water, or other solvents present in solution.

In another embodiment, the latent catalyst described herein is a carbamate salt made by the reaction of a hydroxide base with a multifunctional isocyanate, where the reaction is overindexed on the hydroxide. That is, the reaction includes excess hydroxide to ensure complete conversion to carbamate. Any excess hydroxide remaining after reaction would be titrated with the addition of acid to remove excess base from the system. In an embodiment, the excess hydroxide is present in an amount of up to about 10%, preferably less than 10%, more preferably the smallest excess that is practical to consume all the isocyanate.

The latent catalyst described herein is used to prepare coating compositions, including two-component coating compositions. In an aspect, the coating composition is made by reacting the latent catalyst with a crosslinkable polymer composition through a Michael addition reaction. The polymer composition includes at least one crosslinkable resin component, but may further include non-functional resins, resins with functionality other than required for Michael addition, and the like.

The Michael addition reaction involves the nucleophilic addition of a carbanion or other nucleophile to an electron-deficient ethylenic compound. The nucleophile is referred to as a Michael addition (MA) donor and can be any organic compound that contains at least one active hydrogen and at least one electron withdrawing group such as, for example, —CN, —COOR, —COR, and the like. Michael addition (MA) acceptors are typically ethylenically unsaturated compounds with a double bond that can be activated by a carbonyl group in the alpha position.

Suitable examples of MA donors include, without limitation, dialkyl malonates (e.g., dimethyl malonate, diethyl malonate, and the like), cyanoacetates (e.g., methyl cyanoacetate, ethyl cyanoacetate, and the like), chloroacetates, acetoacetates, propionyl acetates, malononitrile, acetonitrile, acetylacetone, dipropionyl methane, and the like, and mixtures or combinations thereof. Preferred examples of MA donors include, without limitation, malonate or acetoacetate group containing oligomeric and polymeric compounds such as, for example, polyesters, polyurethanes, polyacrylates, epoxy resins, polyamides, and polyvinyl resins containing malonate or acetoacetate functional groups in the main chain, pendant, or both.

Suitable examples of MA acceptors include, without limitation, esters of (meth)acrylic acid, i.e. a (meth)acrylate functional compound derived from the reaction of an hydroxyl functional compound (i) with (meth)acrylic acid or its ester derivatives (ii), wherein the hydroxyl functional compound can be mono-, di-, or polyfunctional and has as a backbone that contains an aliphatic, cycloaliphatic or aromatic chain, a (poly)epoxy, (poly)ether, (poly)ester for example (poly)caprolactone, (poly)alkyd, (poly)urethane, (poly)amine, (poly)amide, (poly)carbonate, (poly)olefin, (poly)siloxane, (poly)acrylate, halogen (e.g. fluorine), a melamine-derivative, copolymers of any of them, and the like, and mixtures and combinations thereof.

The crosslinkable polymer composition may include one or more MA donor components and one or more MA acceptor components. In a preferred aspect, the crosslinkable polymer composition includes at least one malonate-functional MA donor component and at least one acrylate-functional MA acceptor component. Exemplary crosslinkable compositions are as described in Applicants' co-pending patent application, PCT/US2019/031069, filed May 7, 2019, incorporated herein by reference.

Without limiting to theory, it is believed that the MA acceptor and MA donor components will react via a Michael addition reaction, and thereby help improve cure speed, crosslink density, and hardness development for the coating compositions described herein. The improved cured and increased crosslink density will lead to improved performance characteristics.

The MA donor and the MA acceptor are present in a crosslinkable polymer composition that is reacted with the latent base catalyst described herein to produce a coating composition with optimal cure performance and optimal weathering performance. In an aspect, the crosslinkable polymer composition is one part (e.g. Part A) of a two-component coating composition, with the latent base catalyst described herein as the other part (e.g. Part B).

The coating composition described herein is made by reacting the latent base catalyst (Part B) with the crosslinkable polymer composition (Part A), wherein the ratio of A:B can vary depending on reaction conditions and the end use desired. In an embodiment, the amount of latent base catalyst used herein may vary depending on the properties of the coating composition. Preferably, the composition includes about 0.001 to 1 meq, more preferably 0.02 to 0.07 meq, based on the amount of the resin solids in the composition.

In an embodiment, a non-latent base catalyst may be used alone or in combination with the latent base catalyst described herein to accelerate the Michael addition reaction. Examples of suitable non-latent catalysts include, without limitation, tetrabutyl ammonium hydroxide, ammonium hydroxide, DBU (8-Diazabicyclo[5.4.0]undec-7-ene), DBN (1,5-Diazabicyclo[4.3.0]non-5-ene), and TMG (1,1,3,3-tetramethylguanidine).

Suitable additional examples of non-latent catalysts include, without limitation, salts of non-acidic cations such as $K^+$, $Na^+$, $Li^+$, or weakly acidic cations such as, for example, protonated species of strong organic bases such as, for example, DBU, DBN, and the like, or TMG and the like, paired with a basic anion $X^-$ from an acidic X-H group-containing compound, where X is N, P, O, S or C, and the anion $X^-$ is an MA donor capable of reaction with the MA acceptor (e.g. acrylate), and the anion $X^-$ has a pKa of the corresponding acid X-H that is more than two units lower than the pKa of the majority donor component (e.g. acetoacetate-functional resin). Suitable examples of such salts include, without limitation, salts formed from the reaction of KOH and benzotriazole, TBAH and benzotriazole, or KOH and 1,2,4-triazole, included at a level between 0.001 and 1 meq/gram solid resin. Mixtures or combinations of the above may be used. The preferred non-latent catalyst is a solution of potassium benzotriazolide formed from the reaction of KOH and benzotriazole at an equal molar ratio in ethanol.

Optionally, to extend open-time and potlife, one or more additional components may be included, such as, for example. one or more acidic X'-H groups, where X' is N, P, O, S, or C, where the X' anion is a MA donor capable of reaction with the MA acceptor, and the pKa of the X'-H group is lower than the pKa of the majority MA donor (e.g. acetoacetate-functional resin), preferably more than 2 units lower. Suitable examples include, without limitation, ethylacetoacetate, benzotriazole, succinimide, acetyl acetone, or 1,2,4-triazole, and mixtures or combinations thereof. In a preferred aspect, the component is benzotriazole, present in an amount of between about 0.5 and 5%, more preferably between about 0.5% and 1.5%, based on the total weight of resin solids.

In an embodiment, the coating composition described herein includes an acid-scavenging or pH-buffering component. Suitable examples include, without limitation, metal oxide (e.g., zinc oxide, nanoparticular zinc oxide, magnesium oxide, calcium oxide, strontium oxide, barium oxide, lanthanum oxide, ytterbium oxide, zirconium oxide, and the like), mixed metal oxide (e.g., $MgO-TiO_2$, and the like), zeolites (e.g., cesium-exchanged zeolite, X,Y-Cs-occluded zeolite, and the like), modified mesoporous materials (e.g., MgO-coated mesoporous silica (SBA-15), amino-functionalized mesoporous silica (MCM-41), mesoporous silicon oxynitride, and the like), metal hydroxide (e.g., calcium hydroxide, $Na/NaOH/Al_2O_3$, Na/MgO, and the like), metal nitride, metal oxynitride (e.g., silicon, oxynitride, aluminophosphate oxynitride, zirconophosphate oxynitride, calcined NaNO$_3$, and the like), metal carbonate (e.g., calcium carbonate, sodium carbonate, potassium carbonate, and the like), metal silicate (e.g., calcium silicate, calcium borosilicate, magnesium silicate, Mg—Al hydrotalcite, chrysotile, and the like), metal carboxylate salts (e.g., titanium acetylacetate, and the like), organic metal compounds (e.g., organic zirconate, weak base titanate, tetraalkyl titanate, and the like), amines (e.g., guanidine, aziridine, amidine, triethanolamine, DMP30, and the like), imides (e.g., carbodiimide, and the like), diaza-bicyclo compounds (e.g., DABCO, and the like), and mixtures or combinations thereof.

Accordingly, the coating compositions described herein may be applied over an acidic substrate, such as for example, a metal substrate with a pretreatment applied thereon. Suitable examples of pretreatment include, without limitation, iron phosphate, zinc phosphate, silane, zirconium, and the like. Many other pretreatments are known in the metal pretreatment industry. In a preferred aspect, the metal substrate has an iron phosphate treatment applied thereon.

The coating composition described herein may also include other optional ingredients that do not adversely affect the coating composition or a cured coating composition resulting therefrom. Such optional ingredients are typically included in a coating composition to enhance coating aesthetics; to facilitate manufacturing, processing, handling, and application of the composition; and to further improve a particular functional property of a coating composition or a cured coating composition resulting therefrom. For example, the composition described herein may optionally include adhesion promoters, fillers, catalysts, lubricants, pigments, surfactants, dyes, colorants, toners, coalescents, extenders, anticorrosion agents, flow control agents, thixotropic agents, dispersing agents, antioxidants, adhesion promoters, light stabilizers, and mixtures thereof, as required to provide the desired film properties. Each optional ingredient is preferably included in a sufficient amount to serve its intended purpose, but not in such an amount to adversely affect a coating composition or a cured coating composition resulting therefrom.

In an embodiment, the composition described herein may include resin components that do not undergo Michael addition reaction, in addition to the MA donors and MA acceptors described herein. These additional resin components may have no reactive functional groups or have reactive functional groups that undergo reactions other than the Michael addition reaction.

In an embodiment, the coating composition described herein may include a solvent. Suitable solvents may be aqueous, organic, or mixtures thereof. Suitable examples of organic solvents include, without limitation, aliphatic solvents, aromatic and/or alkylated aromatic solvents (e.g., toluene, xylene, and the like), alcohols (e.g., isopropanol), esters (e.g., methoxy propanol acetate, butyl acetate, isobutyl acetate, and the like), ketones (e.g., methyl ethyl ketone, methyl amyl ketone, and the like), glycol ethers, glycyl ether esters, and mixtures or combinations thereof. In an aspect, the coating composition described herein has a low volatile organic compound (VOC) content, preferably less than 400 g/L, more preferably less than 300 g/L, and most preferably less than 250 g/L.

The compositions described herein also show comparable shelf life and an optimal balance of potlife and dry time relative to conventional polyurethane coatings and knowledge of such coatings in art. In an aspect, the compositions described herein have optimal shelf-life and demonstrate no loss of cure-response or any viscosity increase after storage for at least one week at temperatures of about 120 F (48.8°).

In another aspect, the coating compositions described herein also demonstrate optimal potlife, where the composition takes preferably longer than 60 minutes, more preferably longer than 120 minutes, to double in viscosity after mixing.

In an embodiment, the coating composition described herein demonstrates improved cure response relative to systems without a latent base catalyst. In an aspect, the coating composition described herein has optimal cure response, as assessed by pencil hardness tests after the coating is applied to a substrate and allowed to cure. By optimal cure response is meant that the coating composition is dry to handle in about 1 to 30 minutes, preferably in about 1 to 10 minutes after drying at ambient temperature, including at room temperature of 75 to 77 F (approximately 24 to 25° C.), for example. Optimal cure may also be affected by baking at elevated temperatures, including at about 100 F (37.7° C.), 200 F (93.3° C.), 300 F (148.9° C.), and even higher temperatures. In a preferred aspect, optimal cure response is seen when the coating composition is baked at a temperature of about 150 F (65.5° C.).

The coating composition described herein may be used as a primer or may be part of a primer formulation. When used as a primer or in a primer formulation, the composition described herein may be applied over an untreated substrate, a pretreated substrate, a substrate with a temporary coating applied thereon, and the like.

The coating composition described herein, when used as a primer, demonstrates optimal corrosion resistance. By optimal corrosion resistance is meant that a cured coating derived from the compositions described herein shows creep from scribe of less than 3 mm, preferably less than 2 mm, following salt fog exposure.

The coating composition described herein may be used as a topcoat. In an aspect, a first coating (such as a primer, for example) is applied over an untreated substrate, a pretreated substrate, a substrate with a temporary coating applied thereon, and the like. Then, a second coating (such as a topcoat, for example) is applied over the primer, if needed. In an aspect, the second coating is applied only after the first coating has fully dried or cured. In an alternative aspect, the second coating is applied over the first coating before the first coating has fully dried or cured.

The composition described herein may be used as both a primer and a topcoat as part of a coating system applied to a substrate. In an aspect, a first coating, i.e. the coating composition described herein, is applied as a primer over an untreated substrate, a pretreated substrate, a substrate with a temporary coating applied thereon, and the like. Then, a second coating, i.e. the coating composition described herein, is applied as a topcoat over the primer, if needed. In an aspect, the second coating is applied only after the first coating has fully dried or cured. In an alternative aspect, the second coating is applied over the first coating before the first coating has fully dried or cured.

The coating composition described herein is intended for exterior usage and/or intended to be a weatherable coating, for example as a topcoat or direct-to-metal (monocoat) application, i.e. the cured coating formed from the composition described herein demonstrate optimal weatherability. By optimal weatherability is meant a coating that demonstrates 20° gloss retention of at least 60%, preferably at least 70%, and 60° gloss retention of at least 70%, preferably at least 80%, after 2000 hours of accelerated weathering in a xenon arc weathering chamber. Alternatively, the coating has optimal weatherability if the measured color shift ($\Delta E_{00}$) is less than 1.0, preferably less than 0.5 units.

In an embodiment, the coating composition described herein may be used as a primer, and any topcoat may be applied over the described primer. In an aspect, the topcoat composition is also obtained by a Michael addition reaction. The Michael addition-derived topcoat may be the same or different than the Michael addition-derived primer composition described herein. In another aspect, the topcoat composition may be a component not derived by a Michael addition reaction, but known in the art as a suitable topcoat material, such as a polyurethane topcoat, for example.

Conventionally, Michael addition-derived coating compositions have demonstrated improved cure response relative to traditional primers made with polyurethane, epoxy, non-isocyanate systems, and the like. However, use of such Michael addition-derived coatings has been limited due to poor adhesion to various substrates, and due to a lack of corrosion resistance, particularly when applied as a primer or as a direct-to-metal (DTM) coating on a metal substrate, particularly a pretreated steel substrate. Surprisingly, the Michael-addition derived coating composition described herein may be used as a primer or as a DTM coating with optimal corrosion resistance.

The coating composition of the present invention may be applied to a substrate either prior to, or after, the substrate is formed into an article. In an aspect, the coating composition described herein may be applied on a variety of substrates. Suitable examples include, without limitation, natural and engineered buildings and building materials, freight containers, flooring materials, walls, furniture, other building materials, motor vehicles, motor vehicle components, aircraft components, trucks, rail cars and engines, bridges, water towers, cell phone tower, wind towers, radio towers, lighting fixtures, statues, billboard supports, fences, guard rails, tunnels, pipes, marine components, machinery components, laminates, equipment components, appliances, and packaging. Exemplary substrate materials include, without limitation, wood, plastics, thermosets, metals, metal alloys, intermetallic compositions, metal-containing composites, and combinations of these. Exemplary metal substrates include, without limitation, aluminum, steel, weathering steel, and stainless steel. In a preferred aspect, the substrate is steel, preferably steel with a pretreatment applied thereon.

The coating composition described herein may be applied by any method known in the art. Standard methods of application include, without limitation, such as by brushing, spraying, spin coating, roll coating, curtain coating, dipping, gravure coating, bell application, and/or the like. In the case of two-component thermoset substrates, the coating may be applied via in-mold processes. When the coating composition is applied by spray methods, both conventional air or air-assisted spray equipment, or airless spray equipment may be used. Both electrostatic and non-electrostatic equipment may be used.

The coating thickness of a particular layer and the overall coating system will vary depending upon the coating material used, the substrate, the coating application method, and the end use for the coated article. When used as a primer applied over an untreated or pretreated metal substrate, the thickness of the applied coating film is preferably about 0.05 to 20 mils (1.27 to 500 microns), more preferably 0.4 to 40 mil (10 to 100 micron), and even more preferably 1.0 to 2.5 mils (25 to 70 microns).

EXAMPLES

The invention is illustrated by the following examples. It is to be understood that the particular examples, materials, amounts, and procedures are to be interpreted broadly in accordance with the scope and spirit of the inventions as set forth herein. Unless otherwise indicated, all parts and percentages are by weight and all molecular weights are weight average molecular weight. Unless otherwise specified, all chemicals used are commercially available from, for example, Sigma-Aldrich, St. Louis, Missouri.

Unless indicated otherwise, the following test methods were utilized in the Examples that follow.

Corrosion Resistance (Salt Fog)

The corrosion resistance of cured coatings prepared using the compositions and methods described herein is tested using the salt fog method, as described in ASTM B117 (Standard Practice for Operating Salt Fog Apparatus). Results are expressed by degree of blistering (ASTM D714), rusting (ASTM D610), and creep from scribe (ASTM D1654-08). Creep from scribe is expressed on a scale of 0 to 10, wherein 0 indicates extensive corrosion at the scribe, and 10 indicates the coating is unchanged from exposure to the corrosive environment. Rust ratings for coatings subjected to salt fog exposure in a humid environment are also expressed on a scale of 0 to 10, where 0 indicates complete surface ruse, and 10 indicates no surface rust. Blister ratings are expressed on a scale of 0 to 10, where 0 is excessive blistering and 10 is no blistering.

Corrosion Resistance (Creep)

The corrosion resistance of cured coatings formed from the compositions described herein is also tested by measuring creep after exposure to a corrosive environment, as described in ASTM D1654-08. (Standard Test Method for Evaluation of Painted or Coated Specimens Subjected to Corrosive Environments). A coating is applied to a panel and then cured. The panel is then scribed to metal and exposed to salt fog for a given period of time. Paint loss from the scribe is measured and results are expressed as the amount of creep (in mm) from the scribe. For commercially viable coatings, creep from scribe of 2 mm or less is desired.

Potlife Assessment

The potlife of the coating composition described herein is determined by measuring viscosity of the composition over a given period of time under a given set of conditions, such as for example, at room temperature, or after storage in a hotbox, and the like. In the examples herein, viscosity is determined as follows. A Zahn cup is dipped into a sample of the coating composition and completely filled with the sample. The cup is then lifted out, and the efflux time for the sample is measured in seconds, and reported along with the specific Zahn cup number. The potlife is reported as the time taken for the sample of the coating composition to double in viscosity.

Effective Cure (Hardness)

The effectiveness of cure for a coating may be assessed by measuring the hardness of the cured coating using the pencil hardness method, as described in ASTM D3363 (Standard Test Method for Film Hardness by Pencil Test). Pencils of varying hardness from 6B (softest) to 6H (hardest) are applied to the surface of a cured coating. Results are expressed as the hardest pencil which does not mar or scratch the surface of the cured coating applied to a test panel. Thus, for example, if a coating does not rupture with a 2H pencil but ruptures when a 3H pencil is used, the pencil hardness of the coating is 2H.

Cure Speed (Konig)

The hardness of a cured coating may also be assessed by the Konig pendulum hardness method, as described in ASTM D4366 (Standard Test Methods for Hardness of Organic Coatings by Pendulum Damping Test). A pendulum is allowed to oscillate over a cured coating, and the hardness of the cured coating is expressed as the damping time (in seconds) for the pendulum deflection to slow down to a specific value.

Catalyst Stability

Hardness measurements may also be used to assess the stability of the latent catalyst described herein. The catalyst is stored in a hotbox for a given period of time, after which a cured coating prepared with the catalyst and baked for a given period of time at a given temperature is then tested for hardness using both the pencil hardness method and the Konig pendulum hardness method.

Example 1

Synthesis of Catalyst and Coating Composition

To 3.68 g of tetrabutyl ammonium hydroxide (TBAH) 10% solution in methanol was added 6.59 g of OXSOL 100 and mixed. Then 1.32 g of hexamethylene diisocyanate trimer (HDI trimer) solution was added dropwise with thorough mixing. The ratio of hydroxide to isocyanate-functional groups was maintained at 0.9:1.0, resulting in an excess of isocyanate. Any isocyanate that did not react with hydroxide is believed to have reacted with an excess of methanol in solution.

The 0.9 index catalyst prepared above (part B) was combined with a batch of finished paint (part A) including a malonate functional Michael addition donor component and an acrylate-functional Michael addition acceptor component. Parts and B were mixed in a 10:1 (A:B) ratio to form the inventive coating composition. As a control, a composition is prepared using the same part A above combined with a 6% solution (i.e. a dilute solution) of the latent catalyst (commercially available as ACURE 500 from Allnex) as part B.

Example 2

Cure Performance

The control and inventive coating compositions prepared in Example 1 were applied to pretreated metal test panels at a dry film thickness of about 2 mil (50.8 μm). The cure performance of the coatings was then assessed by allowing the coatings to cure and baking the coatings for a given period of time at a given temperature as indicated below in Table 1, and then testing the cured coatings for pencil and Konig pendulum hardness. Results are shown in Table 1.

TABLE 1

| | Cure Performance of Coating Composition | | | |
|---|---|---|---|---|
| | 10' bake at 150 F. (65.5° C.) | | 30' bake at 150 F. (65.5° C.) | |
| Sample | Pencil hardness | Konig hardness | Pencil hardness | Konig hardness |
| Control | F | 13 | F | 24 |
| Inventive | F | 9 | F | 16 |

Example 3

Stability of Catalyst

To assess stability of the latent base catalyst described herein, the 0.9 index catalyst prepared in Example 1 was put in a hotbox at 120° F. (48.8° C.) for one week. Cure performance of the coating was then assessed as shown in Example 2. For comparison, the control sample as in Example 2 was used. Results for cure performance are shown in Table 2.

TABLE 2

| | Cure Performance of Coating Composition After Hotbox | | | |
|---|---|---|---|---|
| | 10' bake at 150 F. (65.5° C.) | | 30' bake at 150 F. (65.5° C.) | |
| Sample | Pencil hardness | Konig hardness | Pencil hardness | Konig hardness |
| Control | F | 15 | F | 25 |
| Inventive | F | 13 | F | 26 |

Example 4

Potlife

To determine the impact of the latent catalyst described herein on the potlife of the coating composition, the 0.9 index catalyst of Example 1 (part B) was mixed with a batch of the finished paint of Example 1 (part A) in a 10:1 (A:B) ratio. Initial viscosity was measured with a #3 signature Zahn cup, and again after 180 minutes. In addition, the coating composition was placed in a hotbox for 120° F. (48.8° C.) for one week and initial viscosity was measured, followed by viscosity after 180 minutes. Results are shown in Table 3A.

TABLE 3A

| Potlife Measurement After Hotbox | | |
|---|---|---|
| Sample | Initial Viscosity (minutes; Zahn #3) | Viscosity after 180 min (minutes; Zahn #3) |
| Control | 14.8 | 33.69 |
| 1 week hotbox; 120° F. (48.8° C.) | 14.8 | 30.6 |

The effect of water on potlife was also assessed for the coating compositions described herein. A sample of the finished paint of Example 1 (part A) was mixed 10:1 by weight with the 0.9 index catalyst of Example 1 (part B) to make a coating composition. One half is used as a control, with the other half combined with a 2% by weight 1:1 solution of water and acetone. Initial viscosity was measured using a #3 signature Zahn cup and expressed as the time (in minutes) for efflux, with additional viscosity measurements taken at specific time points thereafter. Results are shown in Table 3B.

TABLE 3B

| Potlife Measurement with Water | | | | |
|---|---|---|---|---|
| Sample | Initial Viscosity | Viscosity; 60 min | Viscosity; 120 min | Viscosity; 180 min |
| Control | 14.62 | 17.57 | 24.60 | 33.97 |
| 1% water | 13.72 | 14.72 | 17.40 | 19.40 |

Example 5

Performance Characteristics (Cure Response and Corrosion Resistance)

To determine performance of the coatings described herein, primer compositions A, B, C, and D, including resin components crosslinkable by Michael addition were prepared. Compositions A, B, and C were prepared with the 0.9 index catalyst at the levels shown in Table 4. Composition D was a control prepared with a commercially available latent base catalyst (ACURE 500, Allnex) at the level shown in Table 4.

Each composition was spray-applied to metal test panels at a dry film thickness of about 2.0 mil (50 μm). Each panel was then cured for 10 minutes at 150 F (65.5° C.). Cure response for each sample (in 3-4 replicates for each composition) was assessed using the Konig pendulum hardness test.

To determine corrosion resistance of the coating compositions, samples A, B, C, and D were spray-applied to phosphate-treated cold rolled steel test panels (ACT B1000 P99X) at a dry film thickness of about 1.5 to 2.0 mil (38 to 50 μ), and force-cured for 30 minutes at 150 F (65.5° C.). The panels were then placed in a salt-spray cabinet for 500 hours, as described in ASTM B117. Corrosion resistance was assessed by evaluating blistering, rust, and creep from scribe for each sample. Results are shown in Table 4.

TABLE 4

Performance of Coating Composition

| Sample | Catalyst (Part B) | Catalyst Level (meq/g), based on Part A | Cure speed; Konig Hardness (seconds) | Salt Spray 500 h; creep from scribe (mm) | Salt Spray 500 h; blistering | Salt Spray 500 h; rust |
|---|---|---|---|---|---|---|
| A | Inventive (0.9 index carbamate) | 0.80 | 10 | 0.9 | 10 | 10 |
| B | Inventive (0.9 index carbamate) | 1.60 | 17 | 2.2 | 10 | 10 |
| C | Inventive (0.9 index carbamate) | 2.50 | 27 | 7.1 | 10 | 10 |
| D | Commercial (ACURE 500) | 0.41 | 17 | 1.7 | 10 | 10 |

Comparison of the cure performance and salt-spray results for the inventive composition (Sample B) and the control composition (Sample D) show similar performance.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. The invention illustratively disclosed herein suitably may be practiced, in some embodiments, in the absence of any element which is not specifically disclosed herein.

What is claimed is:

1. A method of preparing a latent catalyst, comprising:
providing a hydroxide-functional component;
providing a multifunctional isocyanate component wherein the multifunctional isocyanate is hexamethylene diisocyanate trimer, hexamethyelene diisocyanate homopolymer, or combinations thereof:
reacting the hydroxide-functional component with the multifunctional isocyanate component to produce a latent catalyst having the structure of general formula (I):

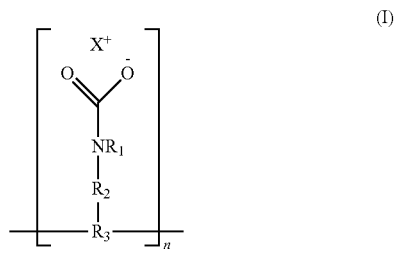

where:
each $X^+$ is independently a non-acidic cation;
each $R_1$ is independently H, C1 to C10 alkyl, aryl, aralkyl, or C1 to C10 substituted alkyl, aryl, aralkyl, or mixture or combinations thereof;
each $R_2$ and $R_3$ is each independently C1 to C10 alkyl, aryl, aralkyl, or C1 to C10 substituted alkyl, aryl, aralkyl, or mixture or combinations thereof; and
n is greater than 1.

2. The method of claim 1, wherein the hydroxide-functional compound is selected from C1-C10 alkyl ammonium hydroxides, aryl ammonium hydroxides, aralkyl ammonium hydroxides, or combinations thereof.

3. The method of claim 1, wherein the hydroxyl-functional compound is C1-C10 alkyl ammonium hydroxide.

4. The method of claim 3, wherein the C1-C10 alkyl ammonium hydroxide is tetrabutyl ammonium hydroxide.

5. The method of claim 1, wherein any multifunctional isocyanate not reacted with the hydroxyl-functional compound reacts with excess solvent in solution.

* * * * *